US009848864B2

(12) United States Patent
Lauchner

(10) Patent No.: US 9,848,864 B2
(45) Date of Patent: Dec. 26, 2017

(54) ADJUSTABLE CANNULA AND METHODS OF USE

(71) Applicant: Kyphon SÀRL, Neuchatel (CH)

(72) Inventor: Craig Lauchner, Mountain View, CA (US)

(73) Assignee: Kyphon SÀRL, Neuchâtel (CH)

( * ) Notice: Subject to any disclaimer, the term of this patent is extended or adjusted under 35 U.S.C. 154(b) by 491 days.

(21) Appl. No.: 14/288,098

(22) Filed: May 27, 2014

(65) Prior Publication Data
US 2015/0342593 A1 Dec. 3, 2015

(51) Int. Cl.
*A61B 17/02* (2006.01)
*A61B 90/30* (2016.01)
*A61B 17/34* (2006.01)

(52) U.S. Cl.
CPC .......... *A61B 17/0293* (2013.01); *A61B 90/30* (2016.02); *A61B 17/3439* (2013.01); *A61B 2090/309* (2016.02)

(58) Field of Classification Search
CPC ............ A61B 17/3415; A61B 17/3417; A61B 17/3421; A61B 17/3423; A61B 17/3431; A61B 17/3439; A61B 2017/3422; A61B 8/4236; A61M 25/0023; A61M 29/00; A61M 2025/0024
See application file for complete search history.

(56) References Cited

U.S. PATENT DOCUMENTS

| 3,788,318 | A |   | 1/1974 | Dusseau et al. |
| 4,397,647 | A | * | 8/1983 | Gordon ................. A61M 25/02 128/DIG. 26 |
| 4,484,913 | A | * | 11/1984 | Swauger ................. A61M 5/00 128/DIG. 26 |
| 5,320,611 | A |   | 6/1994 | Bonutti et al. |
| 5,785,648 | A | * | 7/1998 | Min ......................... A61B 1/32 600/206 |
| 5,792,044 | A |   | 8/1998 | Foley et al. |
| 5,902,231 | A |   | 5/1999 | Foley et al. |
| 5,954,635 | A |   | 9/1999 | Foley et al. |
| 6,007,487 | A |   | 12/1999 | Foley et al. |

(Continued)

OTHER PUBLICATIONS

Medtronic, MeTRx.® II System, 2008, Medtronic Sofamor Danek USA, Inc.

(Continued)

*Primary Examiner* — Anu Ramana

(57) ABSTRACT

A surgical instrument includes a first member including a groove. A second member includes an aperture and teeth configured to slidably engage the groove. A third member is positioned in the aperture and includes a passageway defining a first longitudinal axis and a flange. A fourth member is positioned in the passageway and includes a lip that engages the flange. The lip extends at an acute angle relative to a second longitudinal axis defined by the fourth member. A fifth member is rotatably disposed in the passageway and includes a first end surface that engages a second end surface of the fourth member defined by the lip. In a first configuration, the fourth member extends perpendicular to the first longitudinal axis. In a second configuration, the fourth member extends at an acute angle relative to the first longitudinal axis. Systems and methods are disclosed.

20 Claims, 6 Drawing Sheets

(56) References Cited

U.S. PATENT DOCUMENTS

| | | | |
|---|---|---|---|
| 6,152,871 | A | 11/2000 | Foley et al. |
| 6,162,170 | A | 12/2000 | Foley et al. |
| 6,176,823 | B1 | 1/2001 | Foley et al. |
| 6,206,822 | B1 | 3/2001 | Foley et al. |
| 6,217,509 | B1 | 4/2001 | Foley et al. |
| 6,425,859 | B1 | 7/2002 | Foley et al. |
| 6,520,907 | B1 | 2/2003 | Foley et al. |
| 6,679,833 | B2 | 1/2004 | Foley et al. |
| 6,945,933 | B2 | 9/2005 | Branch et al. |
| 7,196,596 | B2 | 3/2007 | Foley et al. |
| 7,261,688 | B2 | 8/2007 | Smith et al. |
| 7,374,534 | B2 * | 5/2008 | Dalton ............... A61B 17/0218 600/222 |
| 7,473,222 | B2 | 1/2009 | Dewery et al. |
| 7,513,869 | B2 | 4/2009 | Branch et al. |
| 7,524,285 | B2 | 4/2009 | Branch et al. |
| 7,976,463 | B2 | 7/2011 | Dewery et al. |
| 7,981,029 | B2 | 7/2011 | Branch et al. |
| 7,981,030 | B2 | 7/2011 | Smith et al. |
| 7,988,624 | B2 | 8/2011 | Smith et al. |
| 7,993,378 | B2 | 8/2011 | Foley et al. |
| 8,062,217 | B2 | 11/2011 | Boucher et al. |
| 8,246,538 | B2 | 8/2012 | Gorek |
| 8,517,935 | B2 | 8/2013 | Marchek et al. |
| 8,622,897 | B2 | 1/2014 | Raymond et al. |
| 2005/0192485 | A1 | 9/2005 | Branch et al. |
| 2007/0100210 | A1 * | 5/2007 | Selover ................ A61B 17/02 600/199 |
| 2012/0271357 | A1 | 10/2012 | Arthur et al. |

OTHER PUBLICATIONS

Medtronic, MeTRx® System Cases, Product Catlog. 2008, Medtronic Sofamor Danek USA, Inc.

Medtronic, Mast Quadrant™ Retractor System Medial lateral Blades Procedural Solutions Technique, 2009 Medtronic Sofamor Danek USA, Inc.

Medtronic Sofamor Danek, METRx System Surgical Technique, Minimal Access Spinal Technologies, 2004 Medtronic Sofamor Danek USA, Inc.

Medtronic, Direct Lateral Interbody Fusion, DLIF Surgical Technique, 2011 Medtronic Sofamor Danek USA, Inc.

\* cited by examiner though a surgeon may perform a laminectomy in a caudad or cephalad direction. Tunneling may occur by angular movement, which is the same as wagging. When the device is angled or moved, the device may tunnel through tissue without excessive retraction. The device may be angled first, and then the leaves can retract to hold tissue apart.

ADJUSTABLE CANNULA AND METHODS OF USE

TECHNICAL FIELD

The present disclosure generally relates to medical devices for the treatment of musculoskeletal disorders, and more particularly to a surgical system and method for accessing a surgical site to facilitate treatment.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior art technologies.

SUMMARY

In one embodiment, a surgical instrument is provided. The surgical instrument comprises a first member comprising an inner surface defining an arcuate groove. A second member comprises a first portion including an inner surface defining an aperture and a second portion extending from the first portion and including a plurality of spaced apart teeth configured to slidably engage the groove. A third member is positioned in the aperture. The third member comprises an inner surface defining a passageway defining a first longitudinal axis. The inner surface of the third member includes a flange extending perpendicular to the first longitudinal axis. A fourth member is positioned in the passageway and comprises a lip that engages the flange. The lip extends at an acute angle relative to a second longitudinal axis defined by the fourth member. A fifth member is rotatably disposed in the passageway and comprises a first end surface that engages a second end surface of the fourth member defined by the lip. The fourth member is movable between a first configuration in which the first and second end surfaces are spaced apart and the fourth member extends perpendicular to the first longitudinal axis and a second configuration in which the first end surface engages the second end surface and the fourth member extends at an acute angle relative to the first longitudinal axis. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
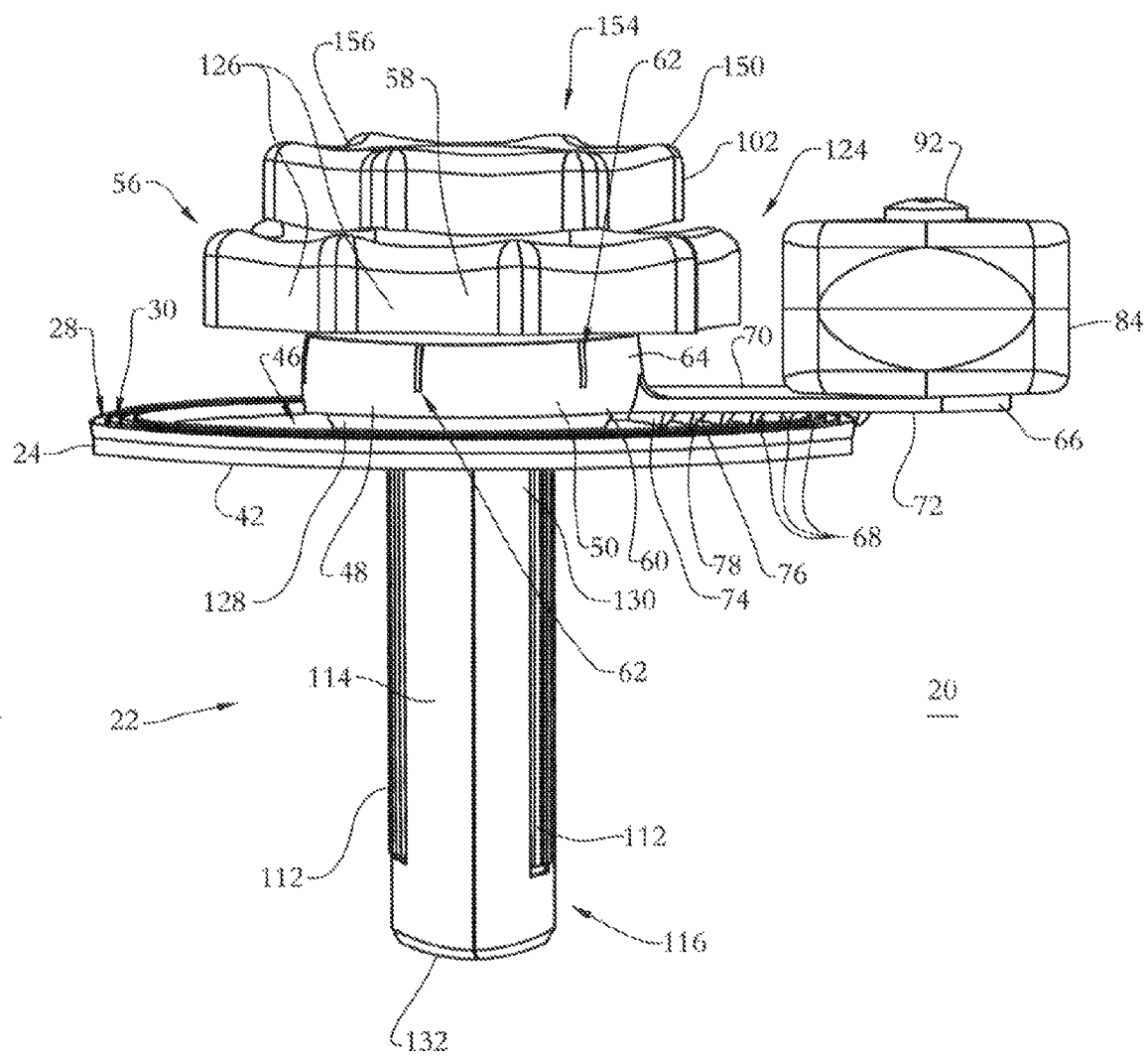
FIG. 1 is a perspective view of components of one embodiment of a surgical system in accordance with the principles of the present disclosure.

The exemplary embodiments of a surgical system and related methods of use disclosed are discussed in terms of medical devices for the treatment of musculoskeletal disorders and more particularly, in terms of a surgical system and method for accessing a surgical site to facilitate treatment. In one embodiment, the surgical system includes a surgical instrument or device that reduces costs and provides unique features that address unmet needs. In some embodiments, the device is made entirely from injection molded parts. In some embodiments, the device is disposable. In some embodiments, the device retracts in a circle or substantially in a circle to provide excellent visualization of a target site. In some embodiments, the device includes three integrated light emitting diodes (LEDs) near a distal tip for illuminating tissues without shadows, thereby increasing effective visualization.

In some embodiments, the device includes expanding leaves for tissue retraction. In some embodiments, the device is circumferentially continuous, eliminating the need for time consuming bleeding control. This feature allows a medical practitioner, such as, for example, a physician to save a good deal of time with cauterizing tools. This feature also allows the medical practitioner to accurately limit the expanded size of the cannula. In some embodiments, the device is circumferentially continuous by having a material, such as, for example, a fabric disposed about blades or members such that the material surrounds the blades as the blades expand and retract. In some embodiments, the device is configured for use by medical practitioners, such as, for example, interventionalists in connection with surgical procedures. In some embodiments, the device is configured for use in procedures in which the patient remains conscious. The device is configured to remain stationary as a patient moves, thus avoiding unintended movement of the surgical device, such as, for example, unintended dorsal movement. In some embodiments, the device includes a wag-and-hold notched ring that adheres to a patient, such as, for example, the skin of the patient. The wag-and-hold feature facilitates one-handed repositioning of the device in 360 degrees for improved visualization. This feature also allows for hands-free positioning of the device. Hands-free positioning is useful, for example, when a procedure, such as, for example, a lumbar decompression, starts on the ipsilateral side and then moves to the contralateral side. Stretching the incision and holding the device requires use of the hand-off in most cases.

In some embodiments, the present disclosure may be employed to treat spinal disorders such as, for example, degenerative disc disease, disc herniation, stenosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including posterior, posterior mid-line, lateral, and/or postero-lateral approaches, and in other body regions. The present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions of bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery, and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-10, there are illustrated components of a surgical system 20 including a surgical device, such as, for example, a retractor or cannula 22 in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancelous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytymosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Cannula 22 includes a first member, such as, for example, a circular ring 24 comprising inner surfaces 26 defining grooves 28, 30. Groove 28 is spaced apart from groove 30. Groove 28 has a radius of curvature that is greater than that of groove 30. Groove 28 is defined by a pair of spaced apart projections 32, 34 and a planar bottom surface 36. Groove 30 is defined by projection 34, a projection 38 that is spaced apart from projection 34 and a planar bottom surface 40. Surfaces 36, 40 each extend parallel to a planar lower surface 42 of ring 22. Projections 32, 34, 38 each extend at an acute angle relative to surface 42 and/or surfaces 36, 40. Projection 32 includes an inner wall 32*a* and an outer wall 32*b*; projection 34 includes an inner wall 34*a* and an outer wall 34*b*; and projection 38 includes an inner wall 38*a* and an outer wall 38*b*. Walls 32*a*, 34*a*, 38*a* extend at the same angle relative to surface 42 and/or surfaces 36, 40. In some embodiments, walls 32*a*, 34*a*, 38*a* extend at an acute angle relative to surface 42 and/or surfaces 36, 40. Walls 32*b*, 34*b*, 38*b* extend at the same angle relative to surface 42 and/or surfaces 36, 40. In some embodiments, walls 32*b*, 34*b*, 38*b* extend at an acute angle relative to surface 42 and/or surfaces 36, 40. In some embodiments, walls 32*a*, 34*a*, 38*a* extend at an angle relative to surface 42 and/or surfaces 36, 40 that is different than that of walls 32*b*, 34*b*, and 38*b*. In some embodiments, walls 32*a*, 34*a*, 38*a* extend at an angle relative to surface 42 and/or surfaces 36, 40 that is greater than that of walls 32*b*, 34*b*, and 38*b*. Ring 24 defines a pathway 46 having a circular cross sectional configuration.

In some embodiments, ring 24 is variously shaped, such as, for example, circular, oval, oblong, triangular, square, polygonal, irregular, uniform, non-uniform, undulating, arcuate and/or variable. In some embodiments, projections 32, 34, 38 each extend at an angle between about 15 degrees and about 75 degrees relative to surface 42 and/or surfaces 36, 40. In some embodiments, walls 32*a*, 34*a*, 38*a* and/or walls 32*b*, 34*b*, 38*b* each extend at an angle between about 30 degrees and about 60 degrees relative to surface 42 and/or surfaces 36, 40. In some embodiments, walls 32*a*, 34*a*, 38*a* and/or walls 32*b*, 34*b*, 38*b* each extend at an angle of about 45 degrees relative to surface 42 and/or surfaces 36, 40. In some embodiments, walls 32*a*, 34*a*, 38*a* and/or walls 32*b*, 34*b*, 38*b* may be disposed at alternate orientations, relative to surface 42 and/or surfaces 36, 40, such as, for example, transverse, perpendicular and/or other angular orientations such as acute or obtuse and/or may be offset or staggered. In some embodiments, surface 42 may have various surface configurations, such as, for example, smooth and/or surface configurations to enhance fixation with tissue, such as, for example, the skin of a patient, such as, for example, rough, arcuate, undulating, porous, semi-porous, dimpled, polished and/or textured. In some embodiments, a removable liner is attached to surface 42. An adhesive is applied to the removable liner to adhere the removable liner to the patient. In some embodiments, pathway 46 may have various cross section configurations, such as, for example, circular, oval, oblong, triangular, rectangular, square, polygonal, irregular, uniform, non-uniform, variable, tubular and/or tapered. In some embodiments, ring 24 is made from plastic, such as, for example, molded plastic.

A second member, such as, for example, a positioning member 48 comprises a portion 50 including an inner surface 52 defining an aperture 54 having a substantially spherical cross sectional configuration configured for disposal of a third member, such as, for example, a holding member 56, as will be discussed. In some embodiments, aperture 54 is concavely curved between a top end 58 of portion 50 and an opposite bottom end 60 of portion 50 such that a middle portion of aperture 54 has a maximum diameter or width that is greater than that of aperture 54 adjacent end 58 or end 60. In some embodiments, aperture 54 is continuously curved between ends 58, 60. In some embodiments, member 48 includes spaced apart slits 62 extending through surface 52 and an opposite outer surface 64 configured to allow aperture 54 to expand and contract as member 56 is inserted into and removed from aperture 54. In some embodiments, member 48 comprises one or a plurality of slits 62. In some embodiments, slits 62 are disposed radially about member 48. In some embodiments, slits 62 are evenly spaced apart from one another. In some embodiments, slits 62 extend parallel to a longitudinal axis defined by member 48. In some embodiments, slits 62 extend through an upper end surface of member 48 without extending through a lower end surface of member 48, as shown in FIG. 1, for example. In some embodiments, slits 62 extend through the lower end surface of member 48 without extending through the upper end surface of member 48. In some embodiments, member 48 includes slits 62 extending through the upper end surface of member 48 and the lower end surface of member 48. In some embodiments, slits 62 extending through the upper end surface of member 48 are aligned with slits 62 extending through the lower end surface of member 48. In some embodiments, slits 62 extending through the upper end surface of member 48 alternate with slits 62 extending through the lower end surface of member 48. In some embodiments, member 48 and/or member 56 are made from plastic, such as, for example, molded plastic.

Member 48 includes a portion 66 extending from portion 50. Portion 66 includes a plurality of spaced apart teeth 68 configured to slidably engage at least one of grooves 28, 30 to couple member 48 with ring 24. Portion 66 includes a planar upper surface 70 and an opposite planar lower surface 72. Surface 70 extends parallel to surface 72. Teeth 68 each extend at an acute angle relative to surface 70 and/or surface 72. Teeth 68 each include side surfaces 74, 76 extending from surface 72. A planar end surface 78 extends between surfaces 74, 76. Surfaces 78 each extend parallel to surface 70 and/or surface 72. Surfaces 74 extend at the same angle relative to surface 70 and/or surface 72. In some embodiments, surfaces 74 each extend at an acute angle relative to surface 70 and/or surface 72. Surfaces 76 extend at the same angle relative to surface 70 and/or surface 72. In some embodiments, surfaces 76 each extend at an acute angle relative to surface 70 and/or surface 72. In some embodiments, surfaces 74 extend at an angle relative to surface 70 and/or surface 72 that is different than that of surfaces 76. In some embodiments, surfaces 74 extend at an angle relative to surface 70 and/or surface 72 that is greater than that of surfaces 76.

In some embodiments, teeth 68 each extend at an angle between about 15 degrees and about 75 degrees relative to surface 70 and/or surface 72. In some embodiments, surfaces 74 and/or surfaces 76 each extend at an angle between about 30 degrees and about 60 degrees relative to surface 70 and/or surface 72. In some embodiments, surfaces 74 and/or surfaces 76 each extend at an angle of about 45 degrees relative to surface lip 134 and/or surface 72. In some embodiments, surfaces 74 and/or surfaces 76 may be disposed at alternate orientations, relative to surface 70 and/or surface 72, such as, for example, transverse, perpendicular and/or other angular orientations such as acute or obtuse and/or may be offset or staggered.

Figure 3:
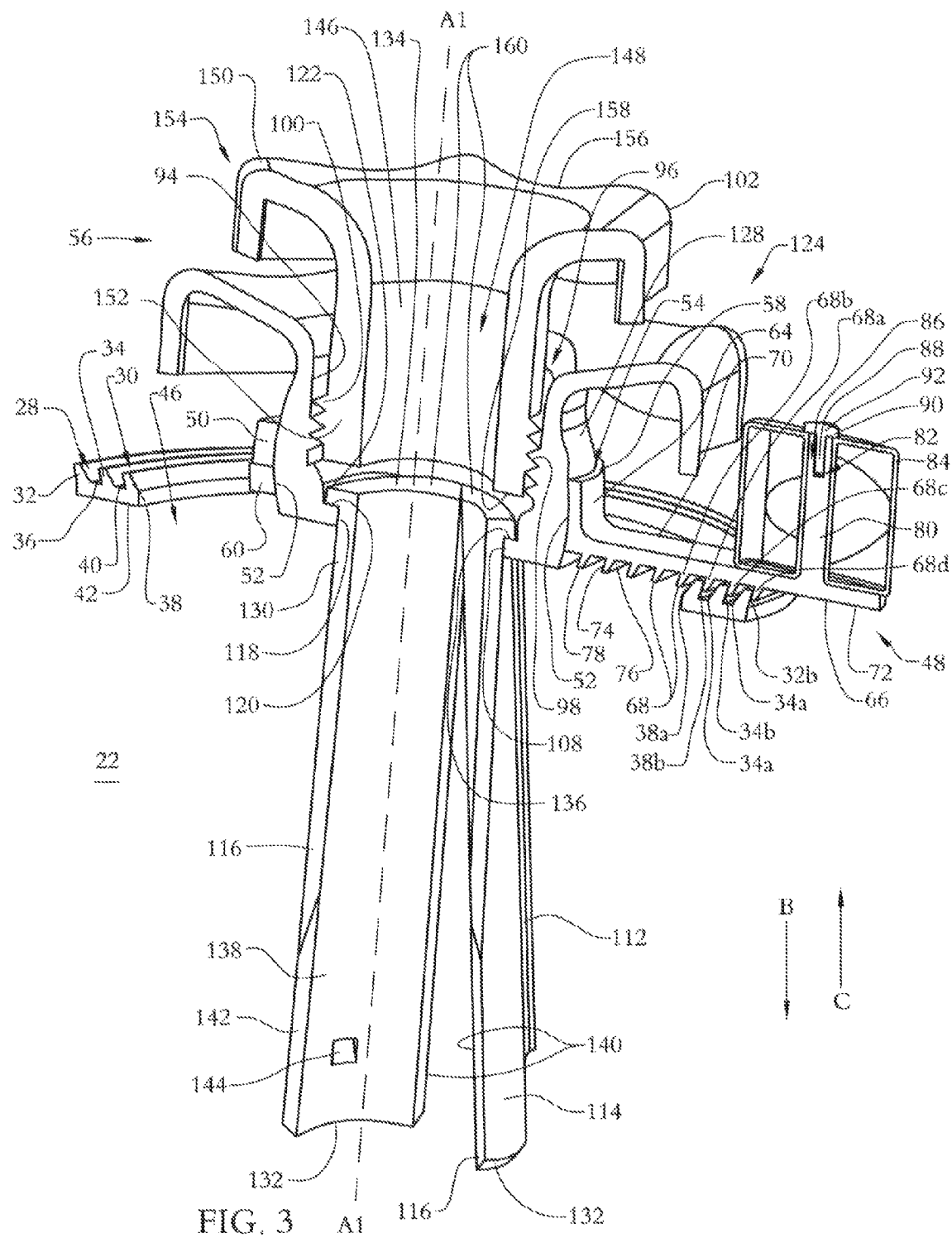
FIG. 3 is a perspective, cross sectional view of components shown in FIG. 1.

As shown in FIG. 3, for example, when a respective tooth 68a is disposed in groove 30, surface 74 of tooth 68a engages wall 38b and surface 76 of tooth 68a engages wall 34a. When surface 74 of tooth 68a engages wall 38b and surface 76 of the tooth 68 engages wall 34a, surface 78 of tooth 68a engages surface 36. When tooth 68a is disposed in groove 30, surface 76 of a first adjacent tooth 68b engages wall 38a. In some embodiments, when surface 76 of tooth 68b engages wall 38a, surface 74 of a second adjacent tooth 68c engages wall 34b and surface 76 of tooth 68c engages wall 32a. When surface 74 of tooth 68c engages wall 34b and surface 76 of tooth 68c engages wall 32a, surface 78 of tooth 68c engages surface 40. In some embodiments, when tooth 68c is disposed in groove 30, surface 74 of a third adjacent tooth 68d engages wall 32b. This configuration allows teeth 68a, 68c to slide within grooves 28, 30 as member 48 moves relative to ring 24 without teeth 68 falling out of grooves 28, 30.

In some embodiments, portion 66 includes an extension 80 extending perpendicular to surface 72 and/or surface 74. Extension 80 extends from surface 70 and includes a blind hole 82. A handle 84 includes an inner surface defining a channel 86 having extension 80 disposed therein such that handle 84 is rotatable about extension 80. A shaft 88 of a pin 90 is disposed in hole 82 such that a head 92 of pin 90 covers channel 86. Head 92 has a maximum width or diameter that is greater than that of channel 86 to prevent head 92 from falling through channel 86. Handle 84 is configured for gripping by a medical practitioner to move member 48 relative to ring 24, such as, for example, to rotate member 48 about an axis defined by pathway 46. In some embodiments, pin 90 can be variously connected with extension 80, such as, for example, monolithic, integral connection, frictional engagement, threaded engagement, mutual grooves, screws, adhesive, nails, barbs and/or raised element.

Member 56 comprises an inner surface 94 defining a passageway 96. Passageway 96 includes a proximal portion and a distal portion. The proximal portion of passageway 96 has a maximum diameter that is greater than that of the distal portion of passageway 96. The proximal portion of passageway 96 includes an interior thread form 98 configured to engage an exterior thread form 100 of a fifth member, such as, for example, a locking member 102, to couple member 56 with member 102, as will be discussed. In some embodiments, member 102 can be variously connected with member 56, such as, for example, monolithic, integral connection, frictional engagement, threaded engagement, mutual grooves, screws, adhesive, nails, barbs and/or raised element. In some embodiments, member 56 and/or member 102 are made from plastic, such as, for example, molded plastic.

Passageway 96 extends through a circular opening 104 in a proximal end of member 56 and a substantially circular opening 106 in a distal end of member 56. Passageway 96 defines a first longitudinal axis A1 extending between the proximal and distal ends of member 56. Opening 106 is defined, at least in part, by an annular flange 108 extending perpendicular to axis A1. In some embodiments, flange 108 includes one or a plurality of slots 110 configured for disposal of a ridge 112 projecting from an outer surface 114 of a fourth member, such as, for example, a blade 116. Slots 110 are disposed radially about flange 108 and are evenly spaced apart from one another. Slots 110 each have a depth that is substantially equivalent to a height of each of ridges 112 such that surface 114 engages an inwardly facing end surface 118 of flange 108. Flange 108 is continuously curved between adjacent slots 110.

In some embodiments, opening 104 and/or opening 106 can have various shape configurations, such as, for example, oval, oblong, square, triangular, rectangular, hexagonal, polygonal, irregular, uniform, non-uniform, variable and/or tapered. In some embodiments, the number of slots 110 in flange 108 is equal to the number of blades 116 of cannula 22. In some embodiments, cannula 22 includes one or a plurality of blades 116. In one embodiment, cannula 22 includes three blades 116. In some embodiments, cannula 22 includes six blades 116. In some embodiments, surface 114 is convexly curved between opposite axial surfaces, such as, for example, planar side surfaces 140, 142. In some embodiments, surface 114 is continuously curved between surfaces 140, 142. In some embodiments, at least one of blades 116 is made from plastic, such as, for example, molded plastic. In some embodiments, at least one of blades 116 is made from stainless steel to provide strength.

Flange 108 includes a top surface 120 that extends perpendicular to axis A1. Surface 120 abuts an inner wall 122 of member 56 that extends perpendicular to surface 120 such that wall 122 is parallel with axis A1. In some embodiments, flange 108 and/or surface 120 may be disposed at alternate orientations, relative to axis A1, such as, for example, transverse, perpendicular and/or other angular orientations such as acute or obtuse, co-axial and/or may be offset or staggered. In some embodiments, wall 122 may be disposed at alternate orientations, relative to axis A1 and/or surface 120, such as, for example, transverse, perpendicular and/or other angular orientations such as acute or obtuse, co-axial and/or may be offset or staggered. In some embodiments, the proximal end of member 56 includes a gripping portion 124 comprising a plurality of notches 126 configured for gripping by a medical practitioner to selectively rotate member 56 about axis A1.

Member 56 is positioned in aperture 54 such that an outer surface 128 of member 56 engages surface 52. In some embodiments, member 56 is rotatably disposed in aperture 54 such that member 56 can pivot within aperture 54 through one or a plurality of planes and/or axes. In some embodiments, surface 128 is convexly curved between a distal end surface of member 56 and portion 124. In some embodiments, surface is continuously curved between the distal end surface of member 56 and portion 124. In some embodiments, the convex configuration of surface 128 and the concave configuration of aperture 54 allow member 56 to rotate within aperture 54 through one or a plurality of planes and/or axes.

Proximal portions of blades 116 are positioned in passageway 96. Blades 116 each extend along a second longitudinal axis A2 between an end 130 and an opposite end 132. Ends 130 each comprise a lip 134 extending at an angle α relative to a respective axis A2. A bottom surface 136 of each lip 134 engages surface 120 of flange 108 to couple blades 116 with member 56. In particular, ridge 112 of a respective one of blades 116 is positioned in one of slots 110 to prevent the blade 116 from rotating relative to member 56. When ridge 112 is positioned in the slot 110, the blade 116 is movable along axis A1 in the direction shown by arrow B and the direction shown by arrow C. Surface 114 slides along surface 118 as the blade moves along axis A1 in the direction shown by arrow B or the direction shown by arrow C. The blade 116 is movable along axis A1 in the direction shown by arrow B until surface 136 engages surface 120. In some embodiments, angle α is an acute angle. In some embodiments, angle α is angle between 45 and 90 degrees. In some embodiments, lip 134 may be disposed at alternate orientations, relative to axis A2, such as, for example, transverse, perpendicular and/or other angular orientations such as acute or obtuse, co-axial and/or may be offset or staggered.

Blades 116 each comprise an inner surface 138 that is concavely curved between axial side surfaces 140, 142. In some embodiments, surface 138 is continuously curved between surfaces 140, 142. In some embodiments, surface 138 is planar or flat and comprises sheet metal. In some embodiments, cannula 22 includes fabric between blades 116 so as to form a sheath or sleeve around blades 116 that allows blades 116 to move between first and second configurations discussed hereinbelow. In some embodiments, surface 138 includes a light source 144, such as, for example a light emitting diode (LED) at end 132. Light source 144 is configured to project light away from surface 138. In some embodiments, light source 144 is embedded between surface 138 and surface 114 such that light source 144 is embedded in a wall thickness of blade 116. In some embodiments, light source 144 is applied to surface 138 such that light source 144 does not extend into surface 138. In some embodiments, light source 144 is bonded or otherwise adhered to surface 138 using a glue or adhesive. In some embodiments, light source 144 extends into surface 138 without extending through surface 114. In some embodiments, all or only a portion of surface 140 and/or surface 142 may be variously configured and dimensioned, such as, for example, planar, concave, polygonal, irregular, uniform, non-uniform, staggered, tapered, consistent or variable. In some embodiments, each blade 116 includes a light source 144.

In some embodiments, blade 116 includes a power source, such as, for example, a battery to provide power to light source 144. In some embodiments, light source 144 is powered by an external power source. In some embodiments, blade 116 and/or light source 144 includes a switch, such as, for example, an on/off switch to move light source 144 between an on position in which light source 144 emits light and an off position in which light source 144 does not emit light.

Member 102 is rotatably disposed in passageway 96 such that thread form 98 engages thread form 100. Rotating member 102 relative to member 56 about axis A1 in a first direction, such as, for example, clockwise or counterclockwise moves member 102 relative to member 56 in the direction shown by arrow B. Rotating member 102 relative to member 56 about axis A1 in a second direction, such as, for example, clockwise or counterclockwise moves member 102 relative to member 56 in the direction shown by arrow C. An inner surface 146 of member 102 defines a lumen 148 that is in communication with passageway 96. Member 102 includes a first end 150 and an opposite second end 152. End 150 includes a gripping portion 154 comprising a plurality of notches 156 configured for gripping by a medical practitioner to selectively rotate member 102 about axis A1. End 152 includes a planar end surface 158 configured to engage top surfaces 160 of lips 134. Surface 158 extends perpendicular to axis A1. In some embodiments, surface 158 may be disposed at alternate orientations, relative to axis A1, such as, for example, transverse, perpendicular and/or other angular orientations such as acute or obtuse, co-axial and/or may be offset or staggered.

In assembly, operation and use, surgical system 20, similar to that described above, is employed, for example, with a minimally invasive surgical procedure for spinal and neurosurgical applications with a patient. For example, during spine surgery, a surgeon will make an incision in the skin of a patient's back over vertebrae to be treated. One or more dilators may be employed to gradually separate the muscles and create a portal through which the surgery may be performed.

Ring 24 is coupled to a patient such that the incision is visible through pathway 46. In some embodiments, ring 24 is positioned relative to the patient such that the incision is centrally located within pathway 46. In some embodiments, a glue or other adhesive material is applied to surface 42 such that the adhesive binds to the skin of the patient to fix ring 24 relative to the patient. In some embodiments, surface 42 includes surface configurations to enhance fixation with skin to prevent movement of ring 24 relative to the patient and/or limit movement of ring 24 relative to the patient, such as, for example, rough, arcuate, undulating, porous, semiporous, dimpled, polished and/or textured.

Figure 2:
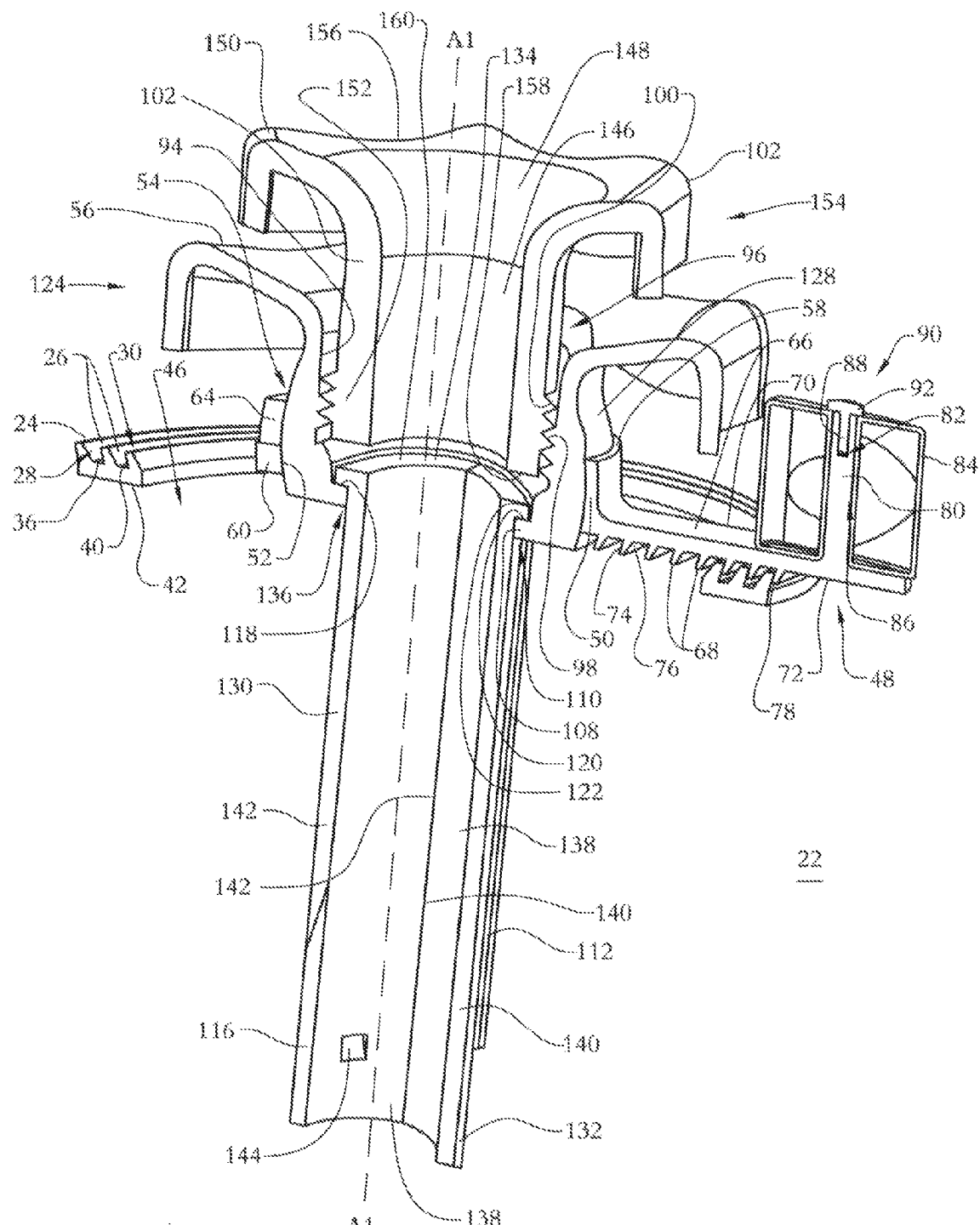
FIG. 2 is a perspective, cross sectional view of components shown in FIG. 1.
Figure 4:
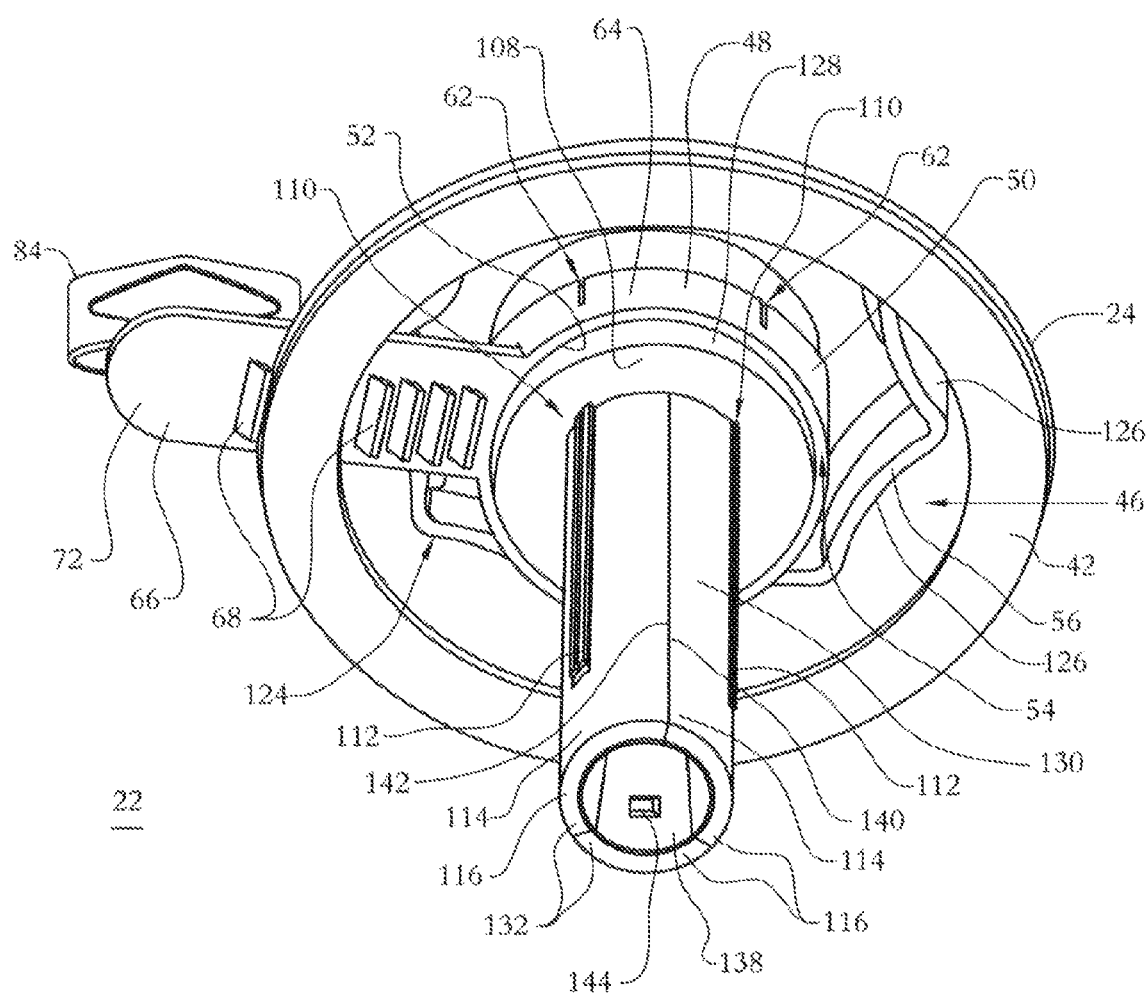
FIG. 4 is a perspective, bottom view of components shown in FIG. 1.

Member 102 is positioned in passageway 96 with blades 116 in a first configuration such that surface 158 is spaced apart from lips 134 and blades 116 each extend parallel to axis A1, as shown in FIG. 2 and FIG. 4. When blades 116 are in the first configuration, surface 140 of a respective blade 116 engages surface 142 of an adjacent blade 116 and surface 142 of the respective blade 116 engages surface 140 of an opposite adjacent blade 116 such that blades 116 form a tubular structure, as shown in FIG. 2 and FIG. 4. That is, when blades 116 are in the first configuration, surfaces 138 define a conduit having a cylindrical cross sectional configuration, as shown in FIG. 4.

Member 56 is coupled with member 48 by positioning member 56 in aperture 54 such that surface 128 engages surface 52. In some embodiments, member 56 is rotatable relative to member 48 when member 56 is positioned in aperture 54. In some embodiments, member 56 is rotated relative to member 48 to a selected orientation or trajectory when member 56 is positioned in aperture 54. For example, member 56 may be rotated relative to member 48 such that an axis defined by aperture 54 extends transverse to axis A1 and/or is offset from axis A1. In some embodiments, member 48 comprises a resilient material such that slits 62 expand from a non-expanded configuration to an expanded configuration as member 56 is inserted into aperture 54 and slits 62 return to the non-expanded configuration after member 56 is inserted into aperture 54.

Blades 116 are inserted through pathway 46 and into the incision. As blades 116 are inserted into the incision, member 48 is positioned relative to ring 24 such that two of teeth 68 are aligned with grooves 28, 30. In one embodiment, shown in FIG. 3, the two teeth 68 are positioned within grooves 28, 30 such that when a respective tooth 68*a* is disposed in groove 30, surface 74 of tooth 68*a* engages wall 38*b* and surface 76 of tooth 68*a* engages wall 34*a*. When surface 74 of tooth 68*a* engages wall 38*b* and surface 76 of the tooth 68 engages wall 34*a*, surface 78 of tooth 68*a* engages surface 36. When tooth 68*a* is disposed in groove 30, surface 76 of a first adjacent tooth 68*b* engages wall 38*a*. In some embodiments, when surface 76 of tooth 68*b* engages wall 38*a*, surface 74 of a second adjacent tooth 68*c* engages wall 34*b* and surface 76 of tooth 68*c* engages wall 32*a*. When surface 74 of tooth 68*c* engages wall 34*b* and surface 76 of tooth 68*c* engages wall 32*a*, surface 78 of tooth 68*c* engages surface 40. In some embodiments, when tooth 68*c* is disposed in groove 30, surface 74 of a third adjacent tooth 68*d* engages wall 32*b*. This configuration allows teeth 68*a*, 68*c* to slide within grooves 28, 30 as member 48 moves relative to ring 24 without teeth 68 falling out of grooves 28, 30. In some embodiments, teeth 68 are inserted into grooves 28, 30 to couple member 48 with ring 24 prior to adhering ring 24 to the skin of the patient.

In some embodiments, teeth 68b, 68c may be removed from grooves 28, 30 and other teeth 68 are positioned relative to grooves 28, 30 in the same manner as teeth 68a-d discussed above. This allows the medical practitioner to adjust the distance of aperture 54 relative to ring 24. For example, if the medical practitioner wishes to position aperture 54 closer to ring 24, teeth 68 closer to aperture 54 are inserted into grooves 28, 30. If, on the other hand, the medical practitioner wishes to position aperture 54 further from ring 24, teeth farther from aperture 54 are inserted into grooves 28, 30. In that member 48 comprises a plurality of uniformly spaced apart teeth 68, this configuration allows the medical practitioner to incrementally adjust the distance between aperture 54 and ring 24.

Once the appropriate teeth 68 are positioned in grooves 28, 30, the medical practitioner may adjust the position of member 48 relative to ring 24 and/or pathway 46 by moving member 48 relative to ring 24 such that teeth 68 translate within grooves 28, 30 without teeth 68 falling out of grooves 28, 30. That is, grooves 28, 30 act as tracks that teeth 68 slide within to move member 48 about an axis defined by pathway 46. In some embodiments, the medical practitioner manipulates handle 84 to rotate member 48 about ring 24. Member 48 may be rotated about ring 24 until member 48 is selectively positioned relative to ring 24 and/or pathway 46.

Figure 5:
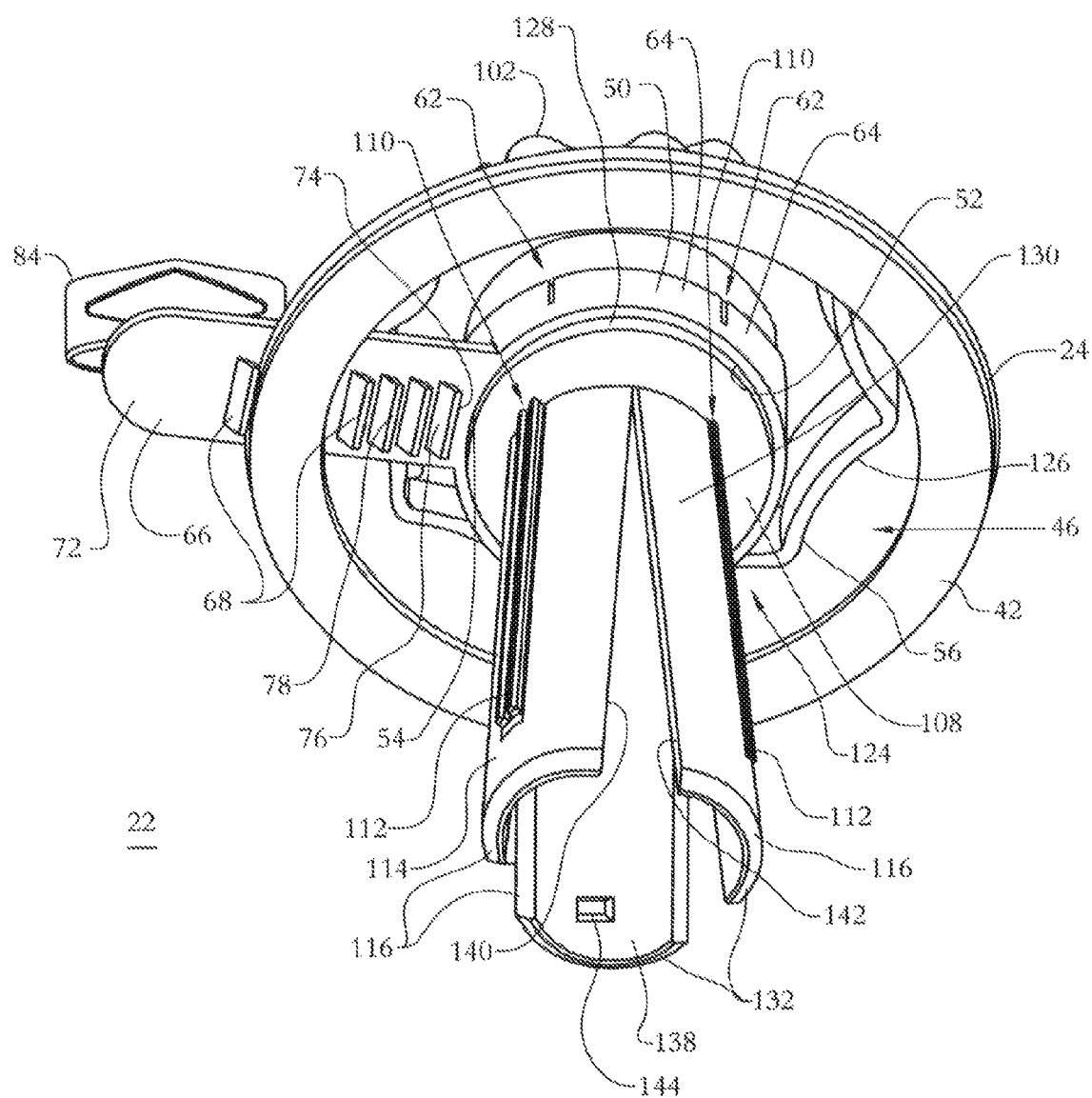
FIG. 5 is a perspective, bottom view of components shown in FIG. 1.
Figure 6:
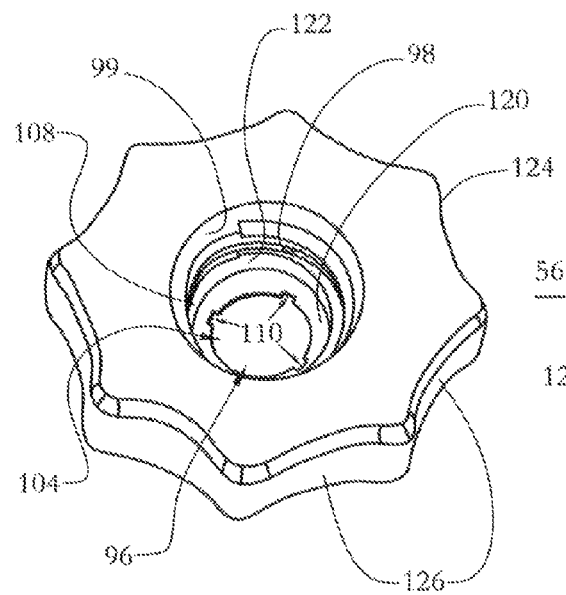
FIG. 6 is a perspective view of a component shown in FIG. 1.
Figure 7:
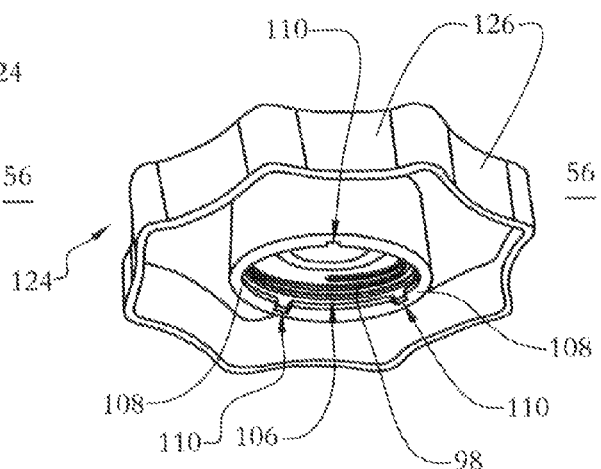
FIG. 7 is a perspective view of a component shown in FIG. 1.
Figure 8:
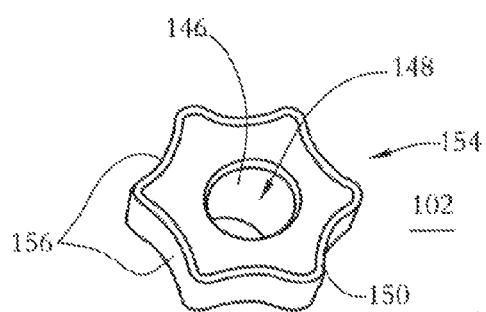
FIG. 8 is a perspective view of a component shown in FIG. 1.
Figure 9:
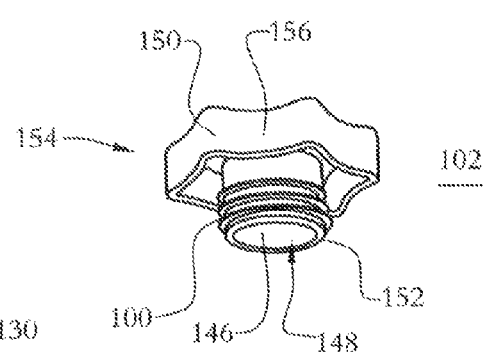
FIG. 9 is a perspective view of a component shown in FIG. 1.
Figure 10:
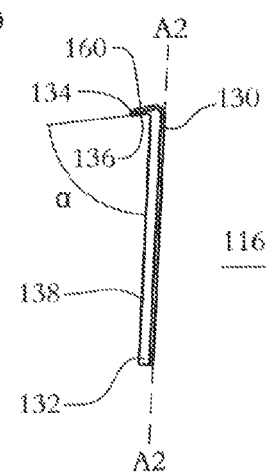
FIG. 10 is a perspective view of a component shown in FIG. 1.

Once member 48 is selectively positioned relative to ring 24 and/or pathway 46, blades 116 are moved from the first configuration to a second configuration such that surface 158 engages lips 134 and blades 116 each extend transverse to axis A1, as shown in FIG. 3 and FIG. 5, to create a passageway or portal to the surgical site. To move blades 116 from the first configuration to the second configuration, member 102 is rotated relative to member 56 about axis A1 in a first direction, such as, for example, clockwise or counterclockwise, causing member 102 to move relative to member 56 in the direction of arrow B. Member 102 is rotated relative to member 56 in the first direction until surface 158 engages surfaces 160 to exert a force on blades 116. Due to the transverse orientation of lips 134, the force causes blades 116 to deflect outwardly away from axis A1 such that blades 116 extend at an acute angle relative to axis A1, as shown in FIGS. 3 and 5. When blades 116 extend at an acute angle relative to axis A1, blades 116 are in the second configuration. When blades 116 are in the second configuration, surface 140 of a respective blade 116 is spaced apart from surface 142 of an adjacent blade 116 at least at ends 132 and surface 142 of the respective blade 116 is spaced apart from surface 140 of an opposite adjacent blade 116 at least at ends 132, as shown in FIGS. 3 and 5.

When blades 116 are in the second configuration, surfaces 114 engage tissue, such as, for example, soft tissue, ligaments, tendons, cartilage and/or bone. Blades 116 space apart tissue and create access and/or a surgical pathway to a surgical site. That is, when blades 116 are in the second configuration, an item, such as, for example, a surgical instrument may be inserted through lumen 148 and passageway 96 and into a conduit defined by surfaces 138. In some embodiments, light sources 144 are in an on position as blades 116 move from the first configuration to the second configuration. In some embodiments, light sources 144 are moved from an off position to an on position after blades 116 are moved from the first configuration to the second configuration. When light sources 144 are in an on position, light sources 144 emit light into the conduit defined by surfaces 138 to aid in visualization to perform a surgical procedure, for example. In some embodiments, light sources 144 are configured to emit light without creating shadows, making cannula 22 useful for imaging purposes, for example. In some embodiments, at least one of blades 116 includes at least one light source 144 at end 130. In some embodiments, at least one of blades 116 includes at least one light source 144 at end 130 and at least one light source 144 at end 132. In some embodiments, at least one of blades 116 also includes at least one light source 144 between ends 130, 132. In some embodiments, blades 116 are inserted into the incision when blades 116 are in the second configuration.

Upon completion of the surgical procedure, member 102 is rotated relative to member 56 in a second direction, such as, for example, clockwise or counterclockwise such that member 102 moves relative to member 56 in the direction shown by arrow C. Member 102 is rotated relative to member 56 in the second direction until surface 158 is spaced apart from surfaces 160 to move blades 116 from the second configuration, shown in FIGS. 3 and 5, to the first configuration, shown in FIGS. 2 and 4. Blades 116 and members 48, 56, 102 may be removed as an assembly by disengaging teeth 68 from grooves 28, 30 and translating blades 116 and members 48, 56, 102 in the direction shown by arrow C. After blades 116 and members 48, 56, 102 are removed, ring 24 may be removed from the patient's body. In some embodiments, after blades 116 and members 48, 56, 102 are removed; ring 24 remains in place and two of teeth 68 are inserted into grooves 28, 30 in the manner discussed above. Blades 116 are inserted into the incision in the first configuration, and are subsequently moved from the first configuration to the second configuration in the manner described above.

It is envisioned that the use of microsurgical and image guided technologies may be employed to access, view and repair spinal deterioration or damage, with the aid of cannula 22. It is contemplated that a surgical procedure may employ other instruments that can be mounted with cannula 22, such as, for example, nerve root retractors, tissue retractors, forceps, cutter, drills, scrapers, reamers, rongeurs, taps, cauterization instruments, irrigation and/or aspiration instruments, illumination instruments, inserter instruments and/or separators, such as, for example, one or more burrs.

Cannula 22 may be employed for performing spinal surgeries, such as, for example, laminectomy, discectomy, fusion, laminotomy, nerve root retraction, foramenotomy, facetectomy, decompression, spinal nucleus or disc replacement and procedures using bone graft and implantable prosthetics including plates, rods, and bone engaging fasteners.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument, comprising:
   a first member comprising an inner surface defining an arcuate groove;
   a second member comprising a first portion including an inner surface defining an aperture and a second portion extending from the first portion and including a plurality of spaced apart teeth that are each configured to slidably engage the arcuate groove;
   a third member positioned in the aperture, the third member comprising an inner surface defining a passageway defining a first longitudinal axis, the inner surface of the third member including a flange extending perpendicular to the first longitudinal axis;
a fourth member positioned in the passageway and comprising a blade portion and a lip that is coupled to the blade portion, the lip engaging the flange and extending at an acute angle relative to a second longitudinal axis defined by the blade portion; and
a fifth member rotatably disposed in the passageway and comprising a first end surface that engages a second end surface of the fourth member defined by the lip,
wherein the fourth member is movable between a first configuration in which the first and second end surfaces are spaced apart and the second longitudinal axis of the blade portion is substantially aligned with the first longitudinal axis and a second configuration in which the first end surface engages the second end surface and the blade portion extends at an acute angle relative to the first longitudinal axis.

2. A surgical instrument as recited in claim 1, wherein the blade portion comprises an inner surface including a light source.

3. A surgical instrument as recited in claim 1, wherein the blade portion comprises an arcuate inner surface including a LED light source embedded within a wall thickness of the blade portion.

4. A surgical instrument as recited in claim 1, wherein the blade portion comprises an arcuate inner surface including a LED light source applied on the arcuate inner surface.

5. A surgical instrument as recited in claim 1, wherein the fourth member comprises a plurality of fourth members each comprising an arcuate inner surface including a light source.

6. A surgical instrument as recited in claim 1, wherein the flange includes a slot, and a ridge that projects from an outer surface of the blade portion being disposed in the slot to prevent rotation of the fourth member relative to the third member.

7. A surgical instrument as recited in claim 1, wherein the arcuate groove comprises two spaced apart circular grooves each having a different radius of curvature.

8. A surgical instrument as recited in claim 1, wherein the arcuate groove is defined by a pair of projections, the projections each having a surface extending at an acute angle relative to a planar bottom surface of the first member.

9. A surgical instrument as recited in claim 8, wherein the teeth each have a surface that extends at an acute angle relative to a planar upper surface of the second member.

10. A surgical instrument as recited in claim 1, wherein:
the inner surface of the first portion is concavely curved;
a portion of an outer surface of the third member is convexly curved; and
the outer surface of the third member engages the inner surface of the first portion such that the third member is rotatable relative to the second member.

11. A surgical instrument as recited in claim 1, wherein:
the passageway includes an internal thread form; and the fifth member comprises an external thread form that engages the internal thread form.

12. A surgical instrument as recited in claim 11, wherein the fifth member is rotated relative to the third member to move the fourth member between the first and second configurations.

13. A surgical instrument as recited in claim 1, wherein the surgical instrument is made entirely from molded plastic.

14. A surgical instrument as recited in claim 1, wherein the first member comprises an inner wall defining a pathway, the first portion, the third member and the fourth member being positioned within the pathway.

15. A surgical method comprising:
providing the surgical instrument of claim 1;
creating an incision;
creating a surgical pathway from the incision to a surgical site;
positioning the fourth member in the pathway with the fourth member in the first configuration; and
moving the fourth member from the first configuration to the second configuration to create a working channel.

16. A method as recited in claim 15, wherein:
the arcuate groove comprises spaced apart first and second circular grooves each having a different radius of curvature; and
the method further comprises removing two of the teeth from the first and second grooves and inserting two other teeth into the first and second grooves to move the fourth member relative to the first member.

17. A method as recited in claim 15, further comprising moving the teeth that slidably engage the arcuate groove slidably along the arcuate groove to move the fourth member relative to the first member.

18. A method as recited in claim 15, further comprising pivoting the third member relative to the second member to adjust a trajectory of the fourth member relative to the first member.

19. A method as recited in claim 15, wherein the fifth member is rotated relative to the third member such that the fifth member translates along the first longitudinal axis to move the fourth member between the first and second configurations.

20. A surgical instrument, comprising:
a ring comprising inner surfaces defining a pair of spaced apart circular grooves each having a different radius of curvature, the grooves each being defined by a pair of projections, the projections each extending at an acute angle relative to a planar bottom surface of the ring, the ring comprising an inner wall defining a pathway;
a positioning member comprising a first portion including an inner surface defining an aperture and a second portion extending from the first portion and including a plurality of spaced apart teeth configured to slidably engage at least one of the grooves to couple the positioning member with the ring, the teeth each extending at an acute angle relative to a planar upper surface of the positioning member, the inner surface of the first portion being concavely curved between opposite first and second ends of the aperture;
a holding member positioned in the aperture to couple the holding member with the positioning member, the holding member comprising an inner surface defining a passageway, the holding member comprising an annular flange that extends from the inner surface and into the passageway, the passageway defining a first longitudinal axis and including an internal thread form, the flange extending perpendicular to the first longitudinal axis, the holding member comprising an outer surface that is convexly curved between opposite first and second ends of the holding member, the outer surface of the holding member engaging the inner surface of the first portion such that the holding member is rotatable relative to the positioning member;
three blades positioned in the passageway and each defining a second longitudinal axis, the blades each comprising a lip extending at an acute angle relative to a respective second longitudinal axis, the blades each comprising an arcuate inner surface including an LED light source; and a locking member rotatably disposed in the passageway such that an external thread form of the locking member engages the internal thread form, a first end surface of the locking member engaging second end surfaces of each of the blades defined by the lips, wherein the first portion, the holding member and the blades are positioned within the pathway, wherein the blades are movable between a first configuration in which the first and second end surfaces are spaced apart and a portion of each of the blades is substantially aligned with the first longitudinal axis and a second configuration in which the first end surface engages the second end surfaces and the portions of the blades each extend at an acute angle to the first longitudinal axis, and the surgical instrument is made entirely from molded plastic.

\* \* \* \* \*

UNITED STATES PATENT AND TRADEMARK OFFICE
CERTIFICATE OF CORRECTION

PATENT NO. : 9,848,864 B2
APPLICATION NO. : 14/288098
DATED : December 26, 2017
INVENTOR(S) : Lauchner Page 1 of 1

It is certified that error appears in the above-identified patent and that said Letters Patent is hereby corrected as shown below:

On the Title Page

In Item (71), under "Applicant", in Column 1, Line 1, delete "Neuchatel" and insert -- Neuchâtel --, therefor.

In the Specification

In Column 4, Line 8, delete "surgery," and insert -- surgery; --, therefor.

In Column 4, Line 50, delete "corticocancelous" and insert -- corticocancellous --, therefor.

In Column 4, Lines 58-59, delete "polytymosine" and insert -- polytyrosine --, therefor.

In Column 5, Line 13, delete "ring 22." and insert -- ring 24. --, therefor.

In Column 7, Line 7, delete "tooth 68" and insert -- tooth 68a --, therefor.

In Column 10, Line 54, delete "tooth 68" and insert -- tooth 68a --, therefor.

Signed and Sealed this
Twenty-sixth Day of June, 2018

Andrei Iancu
*Director of the United States Patent and Trademark Office*